United States Patent
Lin et al.

(10) Patent No.: US 9,658,305 B2
(45) Date of Patent: May 23, 2017

(54) WIRELESS PROSPECTIVE MOTION MARKER

(75) Inventors: Wei Lin, Gainseville, FL (US); Charles Albert Saylor, Gainesville, FL (US); Arne Reykowski, Gainesville, FL (US)

(73) Assignee: KONINKLUJKE PHILIPS N.V., Eindhoven (NL)

( * ) Notice: Subject to any disclaimer, the term of this patent is extended or adjusted under 35 U.S.C. 154(b) by 686 days.

(21) Appl. No.: 14/118,272

(22) PCT Filed: May 16, 2012

(86) PCT No.: PCT/IB2012/052460
§ 371 (c)(1),
(2), (4) Date: Nov. 18, 2013

(87) PCT Pub. No.: WO2012/160486
PCT Pub. Date: Nov. 29, 2012

(65) Prior Publication Data
US 2014/0077811 A1    Mar. 20, 2014

Related U.S. Application Data

(60) Provisional application No. 61/488,858, filed on May 23, 2011.

(51) Int. Cl.
*G01V 3/00* (2006.01)
*G01R 33/565* (2006.01)
(Continued)

(52) U.S. Cl.
CPC ........ *G01R 33/56509* (2013.01); *A61B 5/055* (2013.01); *A61B 5/1127* (2013.01);
(Continued)

(58) Field of Classification Search
CPC .. G01R 33/56509; G01R 33/58; A61B 5/055; A61B 5/1127; A61B 2090/3954; A61B 2017/00694
(Continued)

(56) References Cited

U.S. PATENT DOCUMENTS 4,567,893 A * 2/1986 Charles .............. G01R 33/5676
324/309
4,712,560 A * 12/1987 Schaefer ............ G01R 33/5676
324/309
(Continued)

FOREIGN PATENT DOCUMENTS

JP       03178638 A  *  8/1991
JP       06014905 A  *  1/1994
(Continued)

OTHER PUBLICATIONS

Zaitsev et al., "Magnetic Resonance Imaging of Freely Moving Objects; Prospective Real-Time Motion Correction Using an External Optical Motion Tracking System", Apr. 5, 2006, NeuroImage, pp. 1038-1039.*
(Continued)

*Primary Examiner* — Susan Lee

(57) ABSTRACT

A magnetic resonance system includes a magnetic resonance scanner (8) and a magnetic resonance scan controller (24). A plurality of markers (40, 140) are attached to the subject to monitor motion of a portion of a subject within an examination region. A motion control unit receives motion data from the markers indicative of the motion and controls the magnetic scan controller to adjust scan parameters to compensate for the motion. In one embodiment, the marker (40) includes a substance (44) which resonates at a characteristic frequency in response to radio excitations by the magnetic resonance scanner. A controller (52) switches an
(Continued)

inductive circuit (48, 50) disposed adjacent the substance between a tuned state and a detuned state.

20 Claims, 5 Drawing Sheets

(51) Int. Cl.
*A61B 5/055* (2006.01)
*A61B 5/11* (2006.01)
*G01R 33/58* (2006.01)
*A61B 17/00* (2006.01)
*A61B 90/00* (2016.01)

(52) U.S. Cl.
CPC ............... *A61B 2017/00694* (2013.01); *A61B 2090/3954* (2016.02); *G01R 33/58* (2013.01)

(58) Field of Classification Search
USPC ......... 324/309, 318, 322; 600/414, 415, 421
See application file for complete search history.

(56) References Cited

U.S. PATENT DOCUMENTS

| | | | |
|---|---|---|---|
| 6,584,337 B2* | 6/2003 | Dumoulin | ............... A61B 5/055 324/309 |
| 6,957,098 B1 | 10/2005 | Hyde | |
| 7,295,007 B2 | 11/2007 | Dold | |
| 7,365,334 B1 | 4/2008 | Gordon | |
| 8,098,149 B2* | 1/2012 | Fisher | .................... G01R 33/28 340/539.1 |
| 2002/0118373 A1 | 8/2002 | Eviatar | |
| 2003/0220559 A1 | 11/2003 | Ehnholm | |
| 2006/0241392 A1* | 10/2006 | Feinstein | ............. A61B 5/0006 600/422 |
| 2008/0214923 A1 | 9/2008 | Krueger | |
| 2009/0138019 A1* | 5/2009 | Wasielewski | .......... A61B 17/00 606/87 |
| 2009/0209846 A1 | 8/2009 | Bammer | |
| 2010/0245091 A1* | 9/2010 | Singh | ..................... A61B 5/024 340/573.1 |
| 2010/0264922 A1* | 10/2010 | Xu | ..................... G01R 33/5676 324/309 |
| 2011/0022375 A1* | 1/2011 | Odille | ................ G01R 33/5611 703/13 |
| 2011/0263950 A1* | 10/2011 | Larson | ................... A61B 5/024 600/301 |

FOREIGN PATENT DOCUMENTS

| | | |
|---|---|---|
| WO | 2008142629 A2 | 11/2008 |
| WO | 2009090200 A2 | 7/2009 |
| WO | WO 2010109348 A2 * | 9/2010 ......... G01R 33/5611 |

OTHER PUBLICATIONS

Burl et al "Tuned Fiducial Markers to Identify Body Locations With Minimal Perturbation of Tissue Magnetization" Magnetic Resonance in Medicine, vol. 36, Sep. 1996, p. 491-493.

Zimmermann et al "Use of Fiducial Markers for Motion Corrected MRI" Proc. Intl. Soc. Mag. Reson. Med. 11 (2003) p. 1059.

Ooi, Melvyn B. et al "Prospective Real-Time Correction for Arbitrary Head Motion using Active Markers", Magnetic Resonance in Medicine, vol. 62, 2009, pp. 943-954.

Zaitsev, M. et al "Magnetic Resonance Imaging of Freely Moving Objects: Prospective Real-Time Motion Correction using an External Optical Motion tracking System", NeuroImage, vol. 31, 2006, pp. 1038-1050.

* cited by examiner

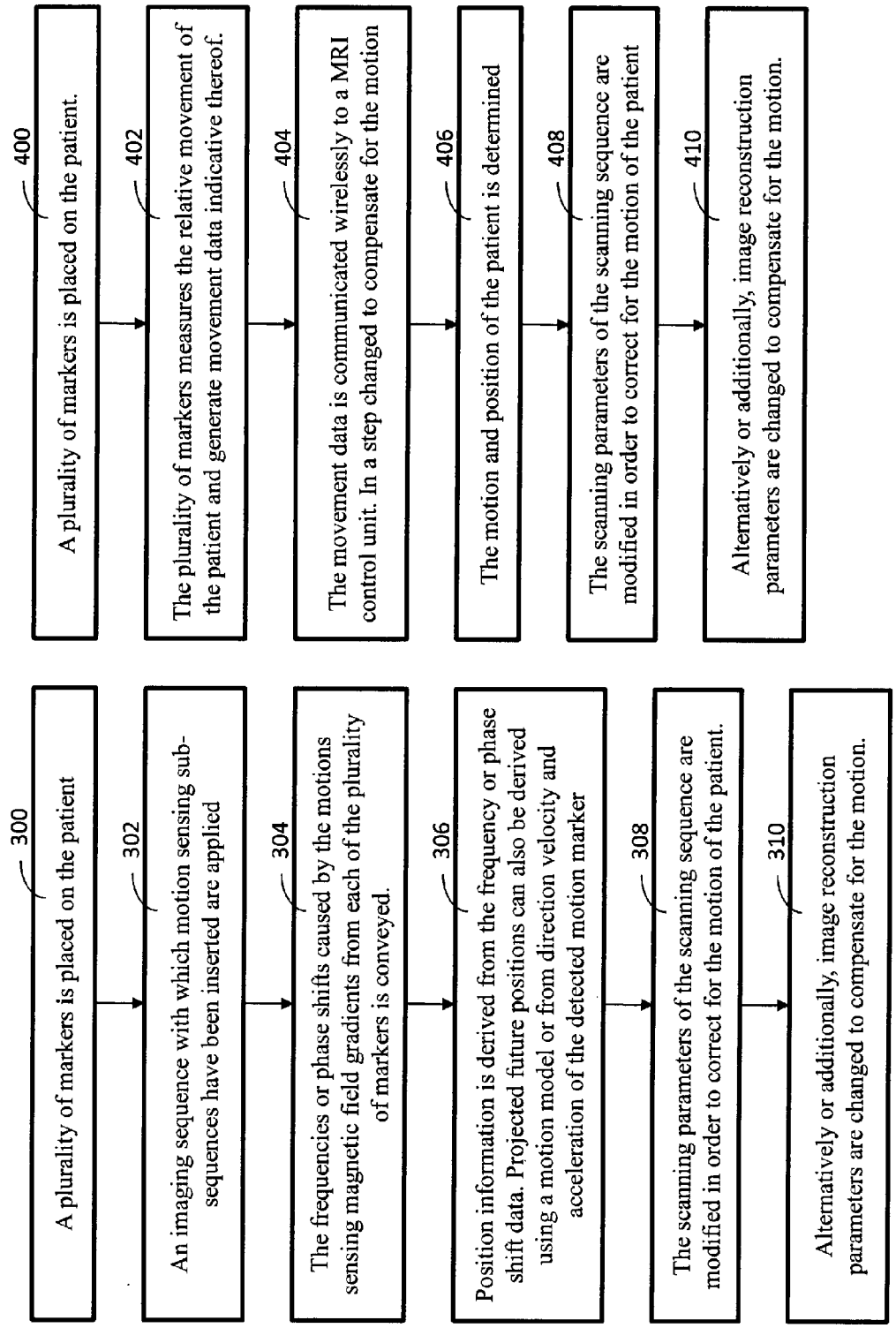

WIRELESS PROSPECTIVE MOTION MARKER

CROSS-REFERENCE TO PRIOR APPLICATIONS

This application is the U.S. National Phase application under 35 U.S.C. §371 of International Application No. PCT/IB2012/052460, filed on May 16, 2012, which claims the benefit of U.S. Provisional Patent Application No. 61/488,858, filed on May 23, 2011. These applications are hereby incorporated by reference herein.

The present application relates to the medical imaging arts, magnetic resonance imaging arts, and related arts. It finds particular application in the wireless determination of position and motion correction and will be described with particular reference thereto.

During magnetic resonance (MR) imaging, it is advantageous for a patient to remain stationary during the scanning procedure. In practice, however, patients may move, and in some cases must move, during the scanning procedure. For example, in shorter scanning procedures, patients must move in order to breathe. In longer scanning procedures, there is a likelihood patients may shift his or her position at some point during the procedure due to fatigue, nervousness, and the like. The likelihood of patient movement generally increases with increased duration of the scanning procedure, and is also enhanced in the case of children, the elderly, or patients with certain diseases (e.g. Parkinson's). Motion correction is also becoming more important due to higher imaging resolution resulting from recent advances in MR imaging methods.

Various methods have been utilized to correct for patient motion during MR scanning procedures including retrospective motion correction techniques and prospective motion correction techniques. Retrospective motion correction techniques correct for motion of a patient after the data has been collected using post image processing techniques. Retrospective motion correction as part of post-processing uses volume registration with voxel interpolation, or signal interpolation in the k-space. Retrospective correction is used to correct for in-plane transformations (e.g., x,y translations) which require simple shifts and rotations of image pixels. But, retrospective correction is weak when correcting through-plane motion (e.g., translation in the slice or axial direction). Interpolation between slices introduces significant partial voluming effects and revolution degradation. The image information lost to through-plane motion would be unable to be entirely recaptured by retrospective correction using interpolation.

Prospective motion correction techniques correct for motion of a patient during the scanning procedure. Prospective motion correction measures current patient location or projects upcoming patient location(s) and adjusts the data acquisition or the image processing to hold the patient immobile in reconstructed image space. When compared with the retrospective motion correction techniques, prospective motion correction techniques can be more accurate and effective for rigid-body motion correction.

However, most existing prospective motion correction methods are not fully compatible with existing MR imaging workflow. For example, one method includes using a camera to monitor and track the movement of a marker placed on a patient during the scanning procedure. This approach has the advantage of being a direct measurement of patient surface position. However, using cameras to monitor the patient is not feasibly if the patient, or the portion of the patient which is of interest is out of the view of the camera, intermittently obscured, or the like. Another method includes using wired sensors to monitor the movement of a patient during the scanning procedure. This method, however, is inconvenient and the wired connections can pose safety hazards during magnetic resonance data acquisition or can become detached so as to lose valuable data. There are also methods based on intrinsic MR signal for prospective motion correction. However, these methods require inserting long navigator modules and delays due to real-time motion detection algorithms into the normal imaging sequence.

The present application provides a new and improved system and method for determining patient position and prospective motion correction which overcomes the above-referenced problems and others.

In accordance with one aspect, a motion compensated magnetic resonance imaging (MRI) method is provided. Motion indication signals are received from a plurality of markers. The patient is scanned using MRI scan parameter to generate MRI resonance data. The MRI resonance data is reconstructed into an image using the MRI scan parameters. A relative position of the patient is determined from the motion indicating signals. At least one of the scanning parameters and image reconstruction parameters is modified to compensate for the motion of the patient.

In accordance with another aspect, a magnetic resonance system includes a magnetic resonance scanner and a magnetic resonance scan controller. The scan controller controls the magnetic resonance scanner to generate magnetic resonance data from a portion of a subject in an examination region, which subject portion is undergoing motion. A plurality of markers is attached to the subject to monitor the motion of the portion of the subject within the examination region. A motion control unit receives motion data from the markers indicative of the motion of the portion of the subject in the examination region and controls the magnetic resonance scan controller to adjust scan parameters to compensate for the motion of the portion of the subject in the examination region.

In accordance with another aspect, the marker includes an element which moves in response to patient motion and a transmitter which transmits signals carrying motion data.

One advantage resides in the real time measurement of patient position.

Another advantage resides in prospective motion correction.

Another advantage resides in the full compatibility with existing MRI workflow.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIGS. 5 and 6 are flowchart diagrams of the operation of the wireless motion correction system in accordance with the present application.

Figure 1:
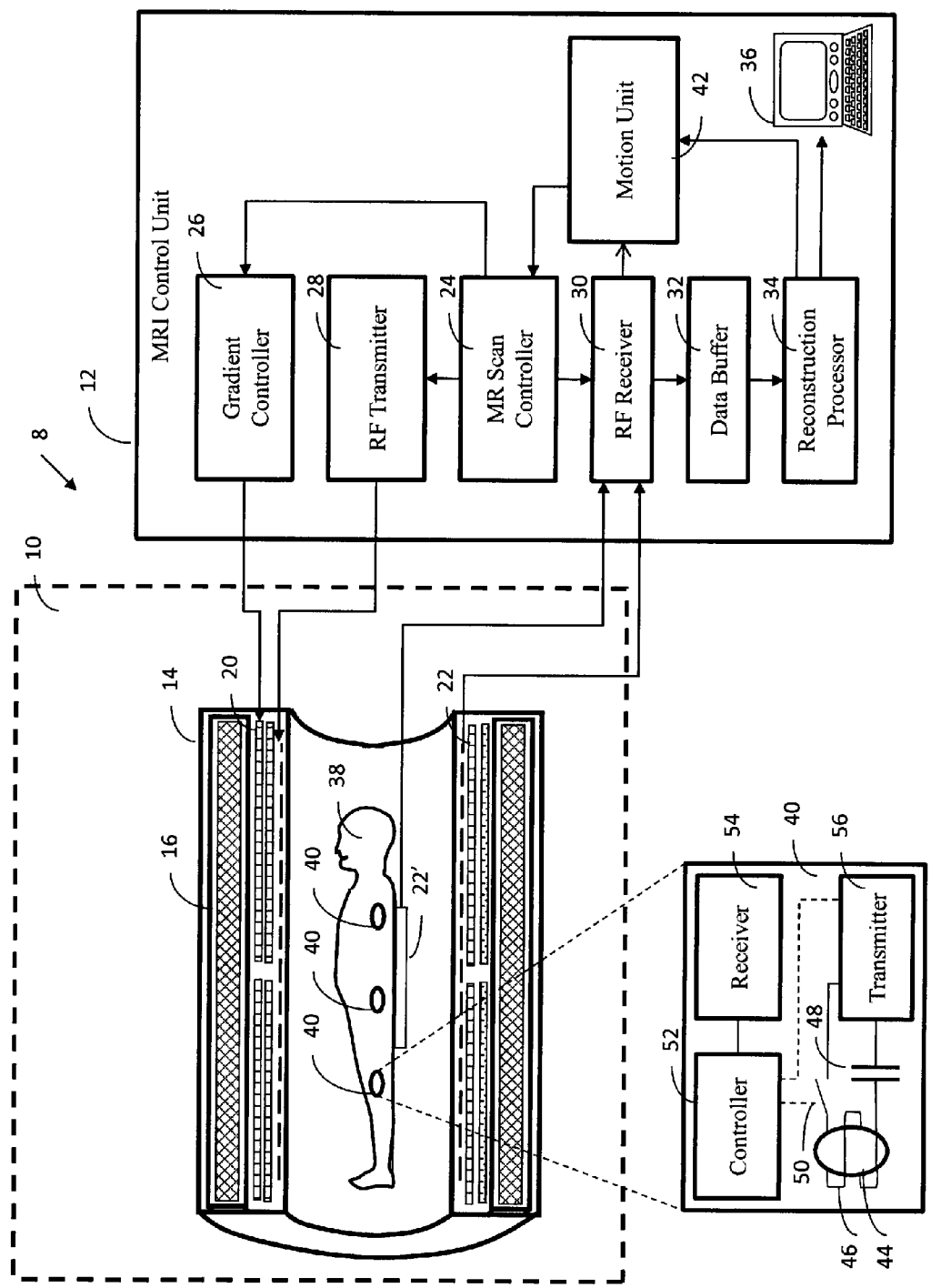
FIG. 1 is a diagrammatic illustration of a wireless motion correction system in accordance with the present application.

FIG. 1 illustrates a magnetic resonance (MR) scanning system 8 for performing prospective motion correction (PMC) using an magnetic resonance imaging (MRI) scanner 14, in accordance with various embodiments described herein. PMC techniques measure changes in geometry due to subject motion during the acquisition of a dynamic series (e.g., during a scan). Subject motion is corrected in real time on the scanner, resulting in an improvement in volume alignment in an image series. The MR system 8 includes wireless disposable devices for measuring motion in real time enabling on-the-fly corrections to be made. Thus, the position and movement of the patient can be detected in real-time and real-time adjustments is made to scanning geometries, reconstruction parameters, and the like as a patient moves during a scan (e.g., 10 minutes, 30 minutes, etc.).

With reference to FIG. 1, illustrated is an RF shielded MRI room 10 located adjacent to an MRI control room which includes an MRI control unit 12 for controlling the operation of an MRI scanner 14. RF shielding is achieved by enclosing the room with copper sheeting, metal foil, plasma, high metallic content (e.g. metal mesh) glass, or other material suitable for RF shielding such as wire mesh. The MRI scanner 14 includes a main magnet 16 which generates a temporally uniform $B_0$ field through an examination region 18. The main magnet can be an annular or bore-type magnet, a C-shaped open magnet, other designs of open magnets, or the like. Gradient magnetic field coils 20 disposed adjacent the main magnet 16 serve to generate magnetic field gradients along selected axes relative to the $B_0$ magnetic field for positionally encoding received signals. A radio frequency coil, such as a whole-body radio frequency coil 22, is disposed adjacent the examination region for inducing resonance and/or receiving RF signals. Optionally, local, surface, or dedicated transrectal RF coils 22' are provided in addition to or instead of the whole-body RF coil 22.

A scan controller 24 controls a gradient controller 26 which causes the gradient coils to apply selected magnetic field gradient pulses across the imaging region, as may be appropriate to a selected magnetic resonance imaging or spectroscopy sequence. The gradient pulses also determine a center of the imaging volume, the orientations of the x, y, and z-coordinates of the imaging volume, and the like. The scan controller 24 also controls an RF transmitter 28 which causes the whole-body or local RF coils to generate magnetic resonance excitation and manipulation $B_1$ pulses. The scan controller 24 also controls an RF receiver 30 which is connected to the whole-body or local RF coils to receive magnetic resonance signals therefrom. The MRI scanner 14 operates under the control of the scan controller 24 in accordance with a selected sequence to excite magnetic resonance.

The received data from the RF receiver 30 is temporarily stored in a data buffer 32 and processed by a magnetic resonance reconstruction processor 34. The magnetic resonance reconstruction processor 34 can perform various functions as are known in the art, including image reconstruction, magnetic resonance spectroscopy, catheter or interventional instrument localization, and the like. Reconstructed magnetic resonance images, spectroscopy readouts, interventional instrument location information, and other processed MR data are displayed on a graphic user interface 36. The graphic user interface 36 also includes a user input device which a clinician can use for controlling the scan controller 24 to select scanning sequences and protocols, and the like.

Three or more markers 40 attached to a patient 38 are utilized to determine the motion and/or the position of the patient 38. A motion unit 42 in the MRI control unit 12 utilizes the markers 40 for prospective motion correction and the real time updating of scanning parameters. The markers 40 are placed on the patient such that movement components along the x, y, and z-axes and the rotational movement components around these axes can be detected. Specifically, the motion unit 42 analyzes position data and, particularly for cyclic motion, uses motion models to measure and predict patient motion during a scan. The markers 40 are tuned to a specific resonance frequency. The markers 40 include a chamber that contains a material 44 which resonates a suitable resonance frequency near but offset from the imaging frequency in presence of the main magnetic field. Suitable materials include a NaCl solution, cooper sulfate doped in water, vitamin E, and the like. The resonance frequency is proportional to the magnetic field strength. Accordingly, in the presence of a magnetic field gradient, the resonance frequency changes along the direction of the gradient. To determine position in the x direction, for example, an x gradient is applied. The resonance frequency then indicates position along the x direction. By sequentially applying x, y, and z-gradients and measuring the frequency, the position of the material along the x, y, and z-directions, i.e. the x, y, and z-coordinates, are readily determined. The x, y, and z-gradients can analogously be used to generate a phase shift along the x, y, and z-directions.

A pick-up coil 46 is tuned to the marker resonance frequency by a capacitor 48 or the like. A component 50, such as a switch, is controlled by a controller 52, e.g. a microcontroller, to tune and detune the pick-up coil 46. A receiver 54 receives control signals from the MR scan controller 24, to tune and detune the pick-up coil 46. The controller 52 also controls a transmitter 56 to transmit the resonance signal. In one embodiment, the transmission and reception is via an RF signal at a frequency sufficiently displaced from the image frequency such that it does not interfere, e.g. Bluetooth. In another embodiment, the transmitter 56 and receiver 54 send and receive optical signals. In another embodiment, the signals are acoustic. In another embodiment, the MR coils 22, 22' send and receive the instructions. In another embodiment, the transmitter is an inductive coupling between the coil 46 and the RF coil 20, 22'. Both analog and digital signals are contemplated.

Position measurement RF and gradient pulses are interspaced in the imaging sequence, for example, an RF excitation followed by three orthogonal gradient pulses. The MR scan controller 24 causes the marker controller 52 to detune the marker pick-up coil 46 during imaging and tune the marker pick-up coil 46 during each of the position measurement gradient pulses and the transmitter 56 to transmit the position indicating signal.

The RF receive coil 22, 22' detects the resonance frequencies produced by the markers 40 and communicates the information to the reconstruction processor 34. The motion unit 42 utilizes the data of the detected resonance frequencies to generate positional information indicative of the position of the markers 40, particularly a position of a region of interest relative to a center of the imaging volume and a rotation relative to the initial coordinate axes of the imaging volume. In one embodiment, the positional information generated from the markers 40 is used to modify the scanning parameters of the scanning sequence in order to correct for the motion of the patient. For example, the imaging region is shifted, rotated, and the like to keep the region of interest in the same relative position and orientation. For another embodiment, the motion correction adjustments are made to the received resonance signals prior to reconstruction.

During a scanning procedure, the marker locating RF pulse and at least three orthogonal projections are applied intermittently in the scanning sequence in order to identify the markers' positions. In some embodiments, an RF pulse of the MR sequence is used for both imaging and marker location purposes. This data is used to update the scanning or image reconstruction parameters in real time. This is accomplished by including intermittent motion detection pulse sequences interleaved with conventional imaging pulse sequences. In response to receiving the motion detection pulse sequences, the specific resonance frequencies delivered by the markers are used to measure the markers 40, hence patient motion during the scan. The scanning and/or image reconstruction parameters are prospectively adjusted during the scan to compensate for the patient motion. For example, the scanning procedure includes a series of image acquisition frames which include a series of interleaved motion detection pulse sequences. Each motion detection sequence includes a plurality of motion detection pulses. During an initial motion detection sequence, the acquired motion detection pulse signals are digitized and stored as reference position/rotation signals. These reference signals indicate the position of the patient at the beginning of the scan, and then serve as a reference against which subsequently acquired motion detection pulse signals can be compared. The specific resonance frequencies received from the markers are processed to calculate the translational movement of the patient along the respective x, y and z axes and the rotational movement of the patient. The movements are calculated by comparing the position/rotation signals acquired during the scan with the reference position/rotation signals acquired at the beginning of the scan. By looking at cyclic movement, acceleration, trajectory, etc. future positions can be predicted.

The MRI control unit 12, the MR scan controller 24, gradient controller 26, the reconstruction process 34, the graphic user interface 36, and the motion correction unit 42 in the illustrative embodiment include at least one processor, for example a microprocessor or other software controlled device configured to execute prospective motion correction software for performing the operations described in further detail below. Typically, the prospective motion correction software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

Figure 2:
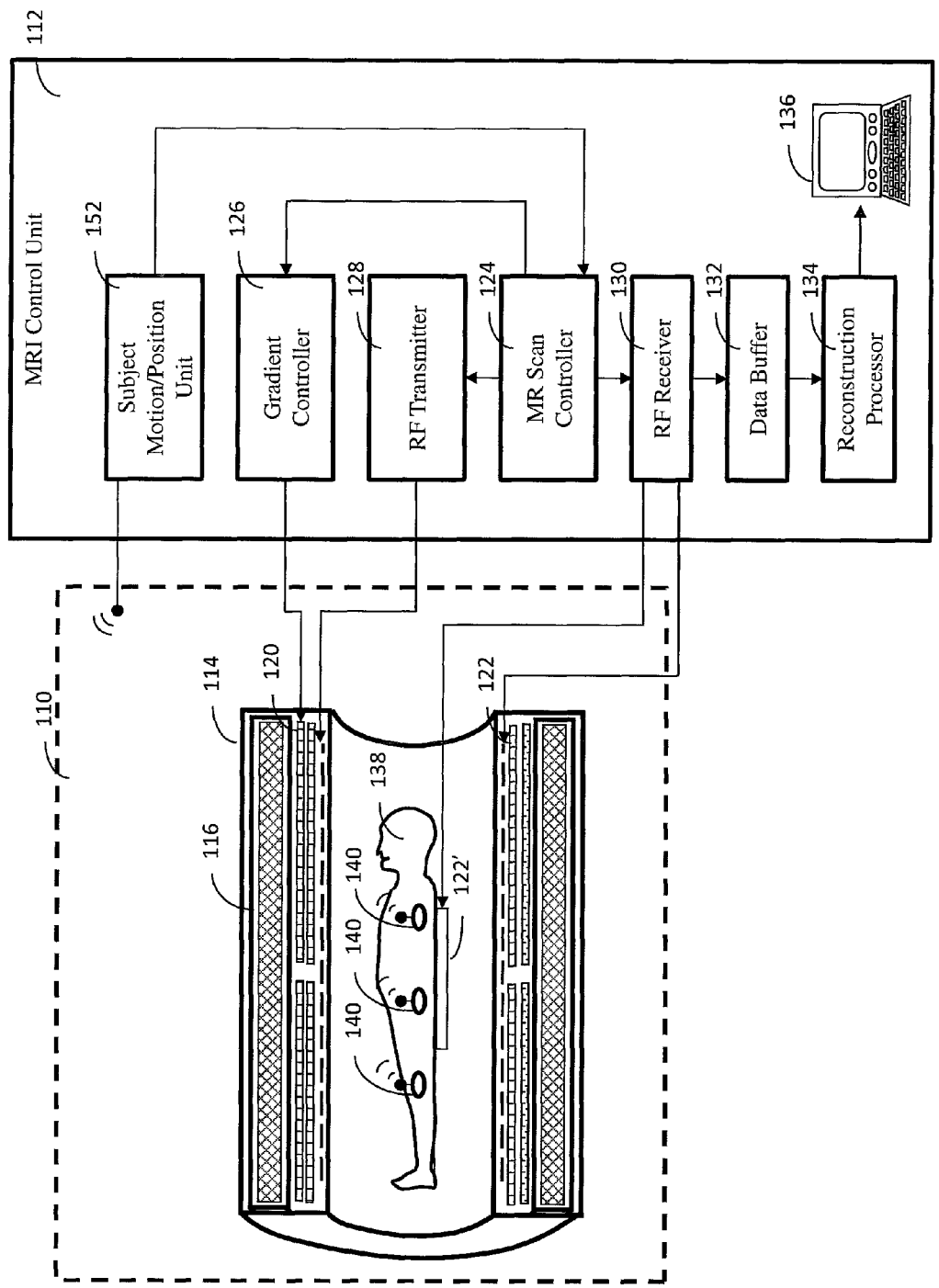
FIGS. 2 and 3 are diagrammatic illustrations of another embodiment of a wireless motion correction system in accordance with the present application.
Figure 3:
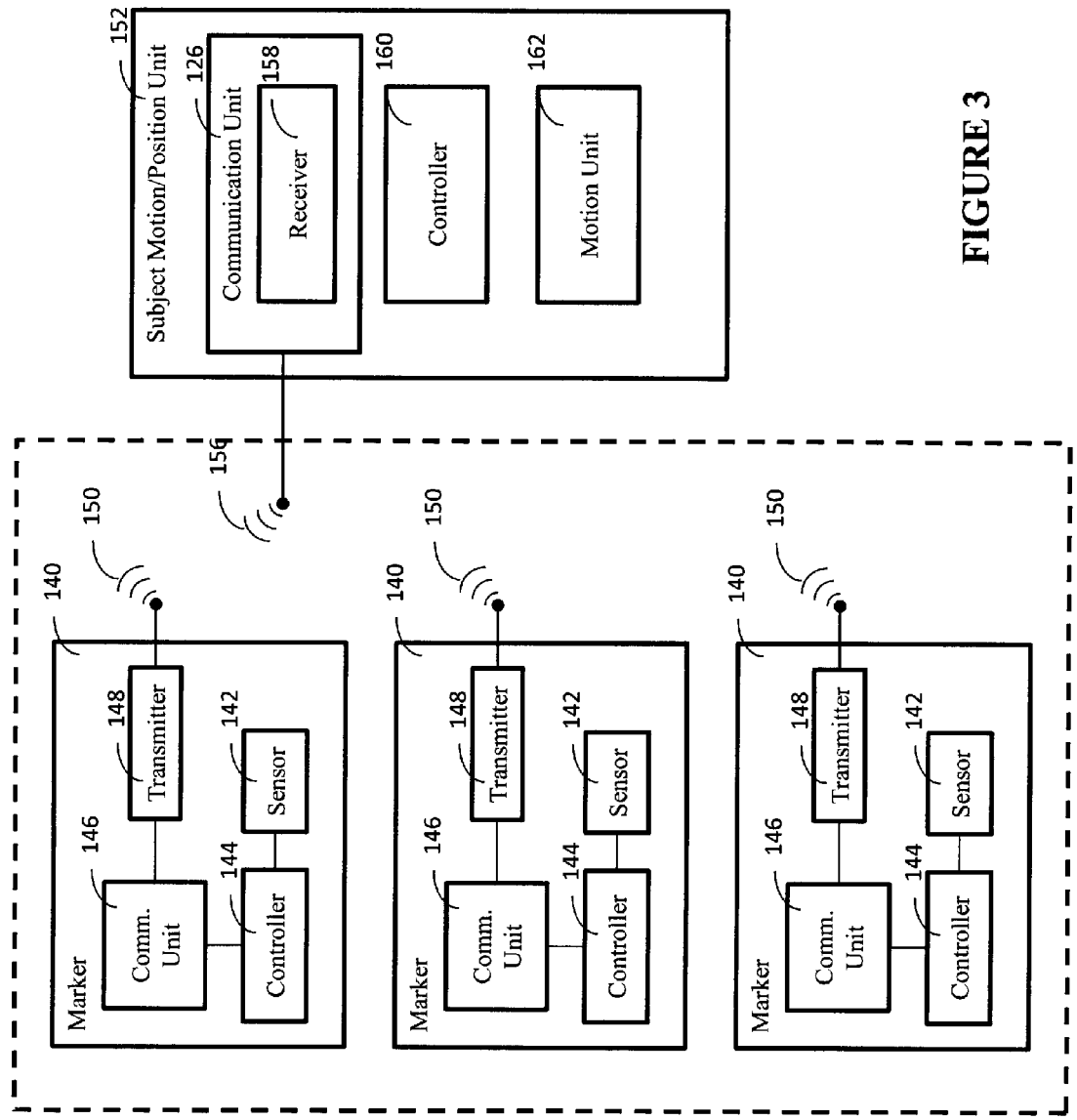

With reference to FIGS. 2 and 3, illustrated is another embodiment of wireless motion system. An RF shielded magnetic resonance imaging (MRI) examination room 110 located adjacent to an MRI control room which includes an MRI control unit 112 for controlling the operation of an MRI scanner 114. The MRI scanner 114 includes a main magnet 116 which generates a temporally uniform $B_0$ field through an examination region 118, gradient magnetic field coils 120 disposed adjacent the main magnet 116 serve to generate magnetic field gradients along selected axes relative to the $B_0$ magnetic field, and a radio frequency coil, such as a whole-body radio frequency coil 122, is disposed adjacent the examination region.

A scan controller 124 controls a gradient controller 126 which causes the gradient coils to apply selected magnetic field gradient pulses across the imaging region, as may be appropriate to a selected magnetic resonance imaging or spectroscopy sequence. The scan controller 124 also controls an RF transmitter 128 which causes the whole-body or local RF coils to generate magnetic resonance excitation and manipulation $B_1$ pulses. The scan controller 124 also controls an RF receiver 130 which is connected to the whole-body or local RF coils 122, 122' to receive magnetic resonance signals therefrom.

The received data from the RF receiver 130 is temporarily stored in a data buffer 132 and processed by a magnetic resonance reconstruction processor 134. Reconstructed magnetic resonance images, spectroscopy readouts, interventional instrument location information, and other processed MR data are displayed on a graphic user interface 136. The graphic user interface 136 also includes a user input device which a clinician can use for controlling the scan controller 124 to select scanning sequences and protocols, and the like.

Three or more wireless markers 140 are attached to the patient 138 to measure the motion of the patient 138 or a volume or organ of interest and generate patient movement data indicative thereof. Each of the markers 140 includes one or more sensors 142 that detect one or more of location, orientation, change in location, change in orientation, and the like of the patient 138. The markers 140 are placed on the patient such that relative movement along the x, y and z-axes and the relative rotational movement of the patient about these axes can be measured. The sensors 142 include accelerometers, gyroscopes, Hall elements, and like that can provide information about the location and movement of the patient 138. For example, an accelerometer in the marker 140 measures the direction and speed of each movement of the patient and generates patient movement data indicative of the motion. Of course, other sensors 142 can be associated with the marker 140, and not all of the above-mentioned sensors 142 have to be associated with a marker 140 at any given time.

The sensors 142 transmit the generated movement data to a controller 144 of the corresponding marker 140. The controller 144 serves as a gathering point for the movement data measured by the sensor 142 and provides temporary storage for the data. The marker 140 may be powered by battery or from power inductively drawn from the MRI sequence. The controller 144 is connected to a communication unit 146 that transmits the generated movement data wirelessly. The generated movement data can be transmitted continuously or periodically. The marker 140 includes a transmitter 148 and an antenna 150 to communicate the generated movement data wirelessly to a subject motion/position unit 152 of the MRI control unit 112. It should be appreciated that while only one antenna 150 is illustrated for each marker 140, more antennas are contemplated. The transmitter 148 can be an RF transmitter working at a frequency of the imaging system, an acoustic transceiver, an IR or other optical transceiver, and the like.

A subject motion/position unit 152 of the MRI control unit 112, in the illustrated embodiment, includes a communication unit 154 which controls a receiver 158 and one antenna 156 extending through the RF shielding of the MRI examination room 110 to receive the generated movement data from the markers 140. The subject motion/position unit antenna 156 is illustrated being positioned, for example, on the RF shielded wall of the MRI examination room 110. It should also be appreciated that the subject motion/position unit antenna 156 is positioned on the RF shielded wall of the MRI examination room 110 such that the communication frequency pass signals through the shield into the control room. Additionally, it should also be appreciated that while only one antenna 156 is diagrammatically illustrated, more antennas are contemplated. The communication links between the transceiver 148 and transceiver 158 may be optic, acoustic, RF, or a combination.

The communication unit 154 transmits the generated movement data to a controller 160 in the subject motion/position unit 152 which serves as a gathering point for the movement data measured by the sensors 142 and provides temporary storage for the data. The controller 160 is connected to a motion correction unit 162 which determines the motion or relative position of the patient 138 from the movement data. The motion unit 142 also analyzes the movement data using one or more generally known prospective motion correction algorithms to compensate for patient movement during a scan. The motion unit 162 utilizes the movement data using one or more generally known prospective motion correction algorithms and generates relative positional information indicative of the position of the patient 38. The positional information generated from the markers 140 is used to modify the scanning parameters of the scanning sequence or the reconstruction parameters in order to correct for the motion of the patient as described above. It may be noted that it is not necessary to determine the absolute position of the marker, only the relative position. An arbitrary position may be selected and the motion information used to correct and generate images in the selected arbitrary position The MRI control unit 112, the MR scan controller 124, gradient controller 126, the reconstruction process 134, the graphic user interface 136, the subject motion/position unit 152, communication unit 158, and the motion correction unit 162 in the illustrative embodiment include at least one processor, for example a microprocessor or other software controlled device configured to execute prospective motion correction software for performing the operations described in further detail below. Typically, the prospective motion correction software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

Figure 4:
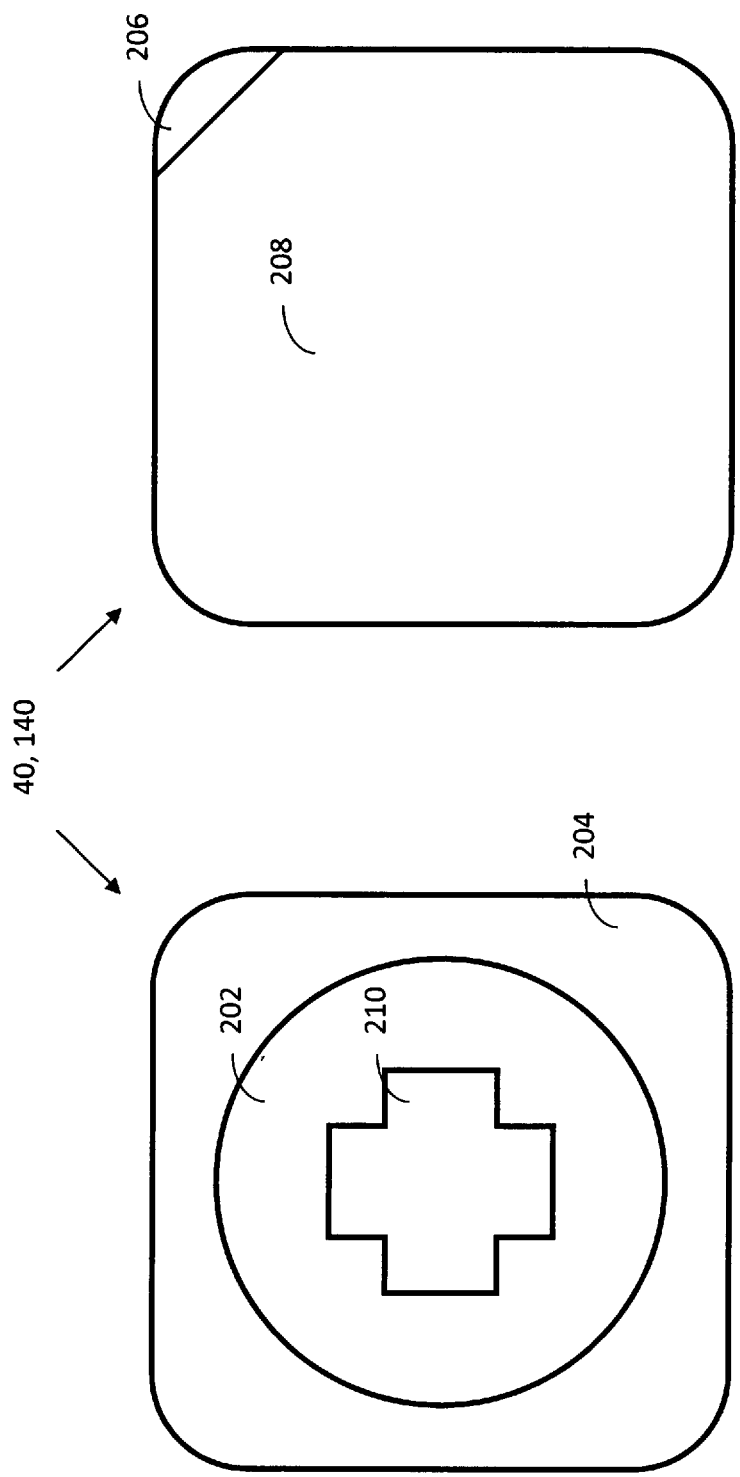
FIG. 4 is an exemplary illustration of a wireless motion marker in accordance with the present application.

With reference to FIG. 4, illustrated is the wireless motion marker 40, 140. The marker includes a motion device 202 which is used to sense the motion of the patient. The motion device includes devices which deliver motion information such as the embodiments of FIG. 1 or 3 as described above. The motion device 202 is attached to a top surface 204 of an adhesive layer 206. A removable backing sheet 210 is applied to the adhesive patch which is removed to attach the markers to the patient. Rather than the motion device 202 being on the top surface, it can be on the lower adhesive surface. The backing sheet is on the axial or patch portion around the motion device. Before the scanning procedure, the removable backing sheet 208 is removed and the marker 40, 140 is placed on the patient in the appropriate location to sense the motion. For example, a plurality of markers may be placed at the lower torso, middle torso, and upper torso of the patient to detect movement of chest of the patient e.g. movement of the diaphragm during breathing. The size, shape, and number of the markers may vary to accommodate the motion to be monitored and the method of wireless prospective motion correction. It should be appreciated that the motion device could have a diameter as small as 1 millimeter but a larger adhesive patch can facilitate manual application. The markers 40, 140 can be packaged in sterile condition inside a package or envelope. It should also be appreciated that the markers 200 are made of materials that are cheap and disposable such that after use of the markers 200, the markers 200 could be thrown away. A visual guide 210 can be applied to the makers to denote the location of the contained motion sensing element. It also contemplated that the makers additionally monitors physiological parameters of the patient such as temperature and heart rate.

With reference to FIG. 5, illustrated is a flowchart diagram of the operation of the wireless prospective motion correction system. In a step 300, a plurality of markers 40 is placed on the patient. In a step 302, an imaging sequence with which motion sensing sub-sequences have been inserted are applied In a step 304, the frequencies or phase shifts caused by the motions sensing magnetic field gradients from each of the plurality of markers is conveyed. In a step 306, position information is derived from the frequency or phase shift data. Projected future positions can also be estimated using a motion model or from direction, velocity, and acceleration of the detected motion marker. In a step 308, the scanning parameters of the scanning sequence are modified in order to correct for the motion of the patient. Alternatively or additionally, in a step 310, image reconstruction parameters are changed to compensate for the motion.

With reference to FIG. 6, illustrated is a flowchart diagram of the operation of another embodiment of the wireless prospective motion correction system. In a step 400, a plurality of markers 140 is placed on the patient. In a step 402, the plurality of markers measures the relative movement of the patient and generate movement data indicative thereof. In a step 404, the movement data is communicated wirelessly to a MRI control unit. In a step 406, the motion and position of the patient is determined. In a step 408, the scanning parameters of the scanning sequence are modified in order to correct for the motion of the patient. Alternatively or additionally, in a step 410, image reconstruction parameters are changed to compensate for the motion.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now clamed to be:

1. A motion compensated magnetic resonance imaging (MRI) method comprising:
    receiving motion indication signals from a plurality of markers;
    scanning a patient using MRI scan parameters to generate MRI resonance data;
    reconstructing the MRI resonance data into an image using the MRI scan parameters;

determining a relative position of at least a volume of interest of the patient from the motion indication signals; and modifying the scanning parameters to compensate for the determined relative motion of the patient.

2. The method according to claim 1, wherein the markers include a resonatable material and at least one of an inductor-capacitance (LC) circuit or a RF micro coil and further including:

during the patient scanning, generating the motion indicating signals such that at least one of a frequency and a phase of the motion indicating signals is indicative of the relative position of the markers.

3. The method according to claim 2, wherein the marker includes a controller which tunes and detunes the LC circuit or RF micro coil and further including:

detuning the LC circuit or RF micro coil during image data collection; and tuning the LC circuit or RF micro coil during relative position data collection.

4. The method according to claim 3, wherein the relative position data collection is interleaved with the image data collection.

5. The method according to claim 1, wherein the markers each include a motion sensor that senses movement of the marker and generate movement data indicative of the sensed motion and further including:

generating the motion indication signals from the movement data such that the signals is indicative of the position of the marker.

6. The method according to claim 1, wherein the markers also include at least one selected from a group consisting of an accelerometer, a gyroscope, and a Hall-effect element to measure movement.

7. The method according to claim 1, wherein the markers transmit the motion indicating signals wirelessly.

8. The method according to claim 1, wherein the markers are placed on the patient such that movement along x, y and z axes and rotational movement of the patient is detected.

9. The method according to claim 1, further including:

adjusting the scan parameters to shift and rotate a scanning volume in accordance with the motion indication signals.

10. A system for prospective motion correction including:
a magnetic resonance imaging (MRI) scanner;
a plurality of markers; and
a data processing device configured to cooperate with the MRI scanner and perform a method as set forth in claim 1.

11. A magnetic resonance system comprising:
a magnetic resonance scanner;
a magnetic resonance scan controller which controls the magnetic resonance scanner to generate magnetic resonance data from a portion of a subject in an examination region, the portion of the subject in the examination region undergoing motion;
a plurality of markers attached to the subject to monitor motion of the portion of the subject within the examination region, wherein each marker further includes:
  a substance which resonates at a characteristic frequency in response to radio frequency excitations by the magnetic resonance scanner;
  an inductive circuit disposed adjacent the substance; and
  a controller which switches the inductive circuit between a tuned state tuned to the characteristic frequency and a detuned state; and
a motion control unit which receives motion data from the markers indicative of the motion of the portion of the subject in the examination region and which controls the magnetic resonance scan controller to adjust scan parameters to compensate for the motion of the portion of the subject in the examination region.

12. The system according to claim 11, wherein each mark includes:
an element which moves in response to patient motion; and
a transmitter which transmits signals carrying motion data.

13. The system according to claim 11, further including:
a receiver which wirelessly receives signals from the MR scan controller to switch the tuned circuit into the detuned state during acquisition of magnetic resonance data and to tune the circuit to the tuned state to acquire the motion data.

14. The marker according to claim 12, wherein the element is a sensor which includes at least one selected from a group consisting of an accelerometer, a gyroscope, a motion sensor, and a Hall-effect element.

15. The marker according to claim 14, further including:
a controller which gathers motion data generated by the sensor and provides temporary storage for the motion data; and
a communication unit which transmits the generated motion data wirelessly to the motion unit.

16. A marker comprising:
an element which moves in response to patient motion; and
a transmitter which transmits signals carrying motion data; wherein the element includes a substance which resonates at a characteristic frequency in response to radio frequency excitations by a magnetic resonance scanner, and further including:
  an inductive circuit disposed adjacent the substance;
  a controller which switches the inductive circuit between a tuned state tuned to the characteristic frequency and a detuned state.

17. The marker as set forth in claim 16, a receiver which wirelessly receives signals from an MR scan controller to switch the tuned circuit into the detuned state during acquisition of magnetic resonance data and to tune the circuit to the tuned state to acquire the motion data.

18. The marker according to claim 16, wherein the element includes at least one selected from a group consisting of an accelerometer, a gyroscope, a motion sensor, and a Hall-effect element.

19. The marker according to claim 18, further including:
a controller which gathers motion data generated by the element and provides temporary storage for the motion data; and
a communication unit which transmits the generated motion data wirelessly.

20. A system for prospective motion correction including:
a magnetic resonance imaging (MRI) scanner; and
a data processing device programmed to control the MRI scanner to generate magnetic resonance data from a portion of a subject in an examination region; and
at least one marker as set forth in claim 16 disposed on a portion of the patient.

* * * * *